United States Patent [19]

Hrib

[11] Patent Number: 4,897,496

[45] Date of Patent: Jan. 30, 1990

[54] METHOD OF SYNTHESIZING FORSKOLIN FROM 9-DEOXYFORSKOLIN

[75] Inventor: Nicholas J. Hrib, Somerville, N.J.

[73] Assignee: Hoechst Roussel Pharmaceuticals, Inc., Somerville, N.J.

[21] Appl. No.: 300,878

[22] Filed: Jan. 25, 1989

Related U.S. Application Data

[62] Division of Ser. No. 147,421, Jan. 25, 1988, Pat. No. 4,822,896, which is a division of Ser. No. 846,550, Mar. 31, 1986, Pat. No. 4,734,513.

[51] Int. Cl.$^4$ .................. C07D 311/78; C07D 407/04
[52] U.S. Cl. ..................................... 549/229; 549/383
[58] Field of Search ................................. 549/383, 229

[56] References Cited

PUBLICATIONS

Anderson et al., JACS, 76, 743, (1954).
Ercoli et al., JACS, 75, 650, (1953).
Vedejs, JACS, 96, 5944, (1974).
House, "Modern Synthetic Reactions", 2nd Ed., Benjamin, Menlo Park, Calif., 1972, pp. 296–321.

*Primary Examiner*—Nicky Chan
*Attorney, Agent, or Firm*—Tatsuya Ikeda

[57] ABSTRACT

A method of regioselectively and stereoselectively synthesizing forskolin (8,13-epoxy-1α,6β,7β,9α-tetrahydroxylabd-14-en-11-one) from 9-deoxyforskolin (8,13-epoxy-1α,6β,7β-trihydroxylabd-14-en-11-one) with a good yield is described. In a preferred embodiment, it comprises an enol ether formation from 8,13-epoxy-1α,6β,7β-trihydroxylabd-14-en-11-one-6,7-carbonate, oxidation of the enol ether with a suitable peroxy acid to obtain 11,12-dehydro-8,13-epoxy-11-methoxy-1α,6β,7β,9α-tetrahydrolabd-14-ene-6,7-carbonate and hydrolysis of the latter under an acidic condition to obtain 8,13-epoxy-1α,6β,7β,9α-tetrahydroxylabd-11-one-6,7-carbonate. As an alternative way of protecting the two hydroxy groups at carbon-6 and carbon-7, they may also be converted to dimethyl acetal during the synthetic sequence. Four compounds produced in the synthetic scheme as intermediates, namely, 9,11-dehydro-8,13-epoxy-11-methoxy-1α,6β,7β-trihydroxylab-14-ene-6,7-carbonate and 11,12-dehydro-8,13-epoxy-11-methoxy-1α,6β,7β,9α-tetrahydroxylabd-14-ene-6,7-carbonate and the corresponding dimethyl acetal compounds are believed to be novel.

4 Claims, No Drawings

METHOD OF SYNTHESIZING FORSKOLIN FROM 9-DEOXYFORSKOLIN

This is a division of Ser. No. 147,421, filed 1/25/88, now U.S. Pat. No. 4,822,896, which is a division of Ser. No. 846,550, filed 3/31/86, now U.S. Pat. No. 4,734,513.

The present invention relates to a method of regioselectively and stereoselectively synthesizing forskolin (8,13-epoxy-1α, 6β, 7β, 9α-tetrahydroxylabd-14-en-11-one) from 9-deoxyforskolin (8,13-epoxy-1α, 6β, 7β-trihydroxylabd-14-en-11-one).

During the isolation of forskolin (formula I) from Coleus forskohlii, a significant amount (about 10–50% of forskolin) of 9-deoxyforskolin (formula II), a biologically less active diterpene of related structure, is also obtained as a byproduct. Since forskolin is a pharmacologically useful compound, for instance as a hypotensive agent (see for example Bajwa et al. U.S. Pat. No. 4,134,986), it is useful to develop a facile method of stereoselectively synthesizing forskolin from 9-deoxyforskolin with a good yield.

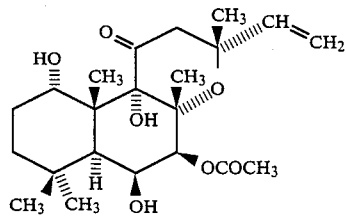

(I) forskolin

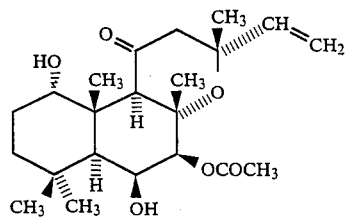

(II) 9-deoxyforskolin

I have developed a facile method of converting 9-deoxyforskolin to forskolin with a complete stereospecificity at 9-carbon and good protection of the existing functionalities. The synthetic method of this invention is amenable to large scale applications and hence will substantially increase the availability of forskolin for commercial applications. Certain compounds synthesized as intermediate compounds in the synthetic scheme of this invention are novel and of course useful, and they constitute another aspect of this invention.

Those skilled in the art will appreciate that since 9-deoxyforskolin contains various functionalities, it is a difficult task to carry out a particular synthesic conversion without adversely affecting other functionalities and that regioselective and stereoselective conversion is generally a difficult task.

The following numbering system is used throughout the specification and the appended claims for the forskolin skeleton:

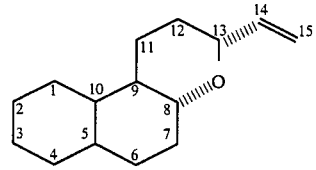

A dashed line (----) indicates that the substituent is projected below the average plane of the six-membered ring to which it is attached and is denoted as alpha (α), whereas a heavy line (◄) indicates that the substituent is projected above the average plane of said six-membered ring and is denoted as beta (β).

The synthetic method of this invention will be described first with reference to a preferred embodiment in which two adjacent hydroxy groups at carbon-6 and carbon-7 are protected by the formation of a carbonate linkage during the synthetic sequence, and then with reference to an alternative embodiment in which the hydroxy groups are protected by the formation of a dimethyl acetal linkage. The overall synthetic scheme used in the preferred embodiment is depicted schematically in FIG. 1.

FIG. 1. Reaction Scheme

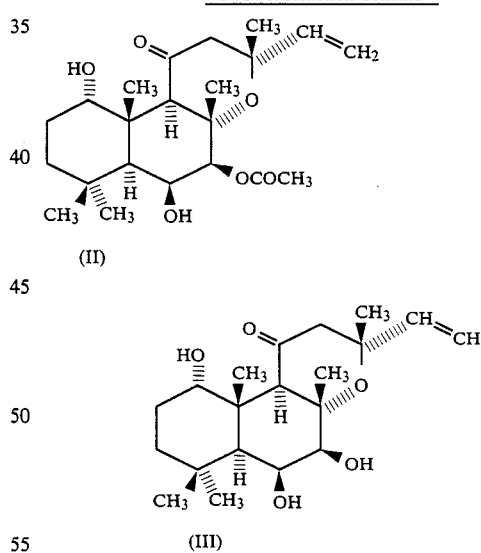

(II)

(III)

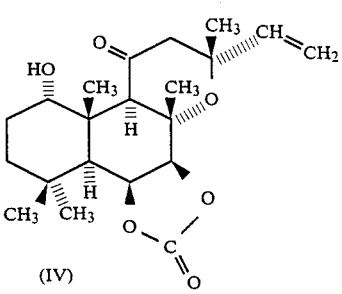

(IV)

-continued
FIG. 1. Reaction Scheme

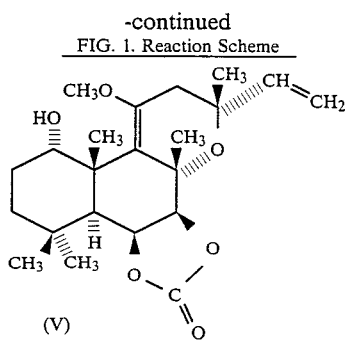
(V)

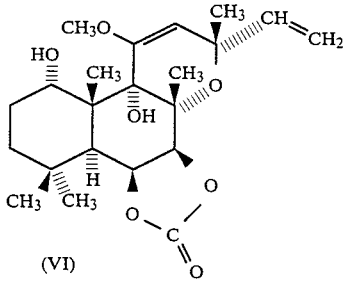
(VI)

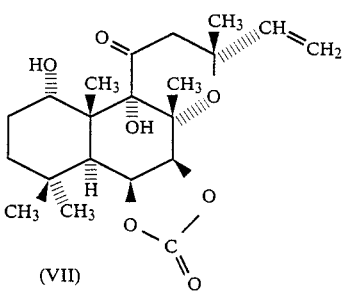
(VII)

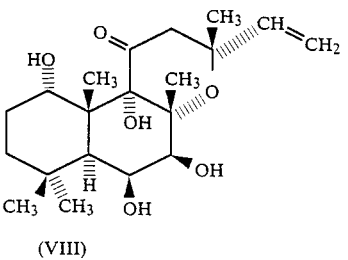
(VIII)

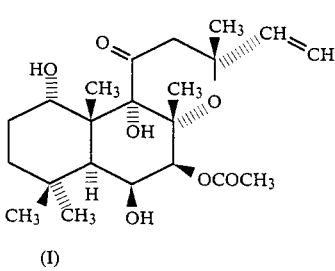
(I)

STEP A

Compound II is hydrolyzed to afford the compound of formula III depicted in FIG. 1. This hydrolysis is conducted typically in the presence of a sufficient amount of water, potassium carbonate and a suitable medium such as methanol and stirring the reaction mixture at room temperature for several hours.

STEP B

In order to protect the two hydroxy groups at carbon-6 and carbon-7, compound III is converted to a carbonate ester, namely, compound IV. Said carbonate ester formation is conducted typically by reacting compound III with 1,1'-carbonyldiimidazole in the presence of triethylamine and a suitable solvent such as anhydrous toluene. Typically, the reaction mixture is refluxed overnight to a few days.

STEP C

Compound IV is converted regioselectively (position-selectively) to the enol ether compound of formula V. This reaction is conducted typically by reacting compound IV with dimethyl sulfate in the presence of potassium hydride and a suitable medium such as anhydrous tetrahydrofuran. Typically, the reaction mixture is stirred at room temperature for several hours under nitrogen atmosphere.

STEP D

Compound V is stereoselectively oxidized to compound VI in which the orientation of the hydroxy group at carbon-9 is alpha. This oxidation is conducted typically by reacting compound V with a suitable peroxy acid such as m-chloroperbenzoic acid in the presence of anhydrous potassium carbonate or the like and a suitable medium such as dichloromethane. Typically, the reaction is conducted at room temperature for a few days.

STEP E

The enol ether compound VI is hydrolyzed under an acidic condition to afford compound VII. Hydrochloric acid is a preferred example of such acid catalyst. Thus, said hydrolysis is typically conducted in a medium prepared, for instance, from 3N aqueous HCl and tetrahydrofuran at 1:3 volume ratio and by stirring the reaction mixture at room temperature overnight.

STEP F

Compound VII is hydrolyzed to afford compound VIII and thereby the protective group for the hydroxy groups at carbon-6 and carbon-7 is removed. It is preferable to conduct this hydrolysis in a basic medium. Thus, said hydrolysis is typically conducted in the presence of sodium bicarbonate or the like, water and a suitable solvent such as methanol and by stirring the reaction mixture at room temperature for a few days.

STEP G

The hydroxy group at carbon-7 of compound VIII is selectively acetylated to afford compound I, namely, forskolin (7β-acetoxy-8,13-epoxy-1α, 6β, 9α-trihydroxylabd-14-en-11-one). Said acetylation is conducted typically by reacting compound VIII with acetic anhydride in a suitable solvent such as anhydrous pyridine. The reaction is conducted typically at ice temperature for several hours.

As an alternative to the synthetic scheme described above in which the two adjacent hydroxy groups at carbon-6 and carbon-7 are protected by the formation of a carbonate linkage, one can also protect the hydroxy groups by the formation of a dimethyl acetal linkage.

Thus, as an alternative to STEP B, one can prepare the acetal compound of formula IV' by reacting compound III with 2,2-dimethoxypropane in the presence of an acidic catalyst, preferably an organic acid such as p-toluene-sulfonic acid or pyridinium p-toluene-sulfonate.

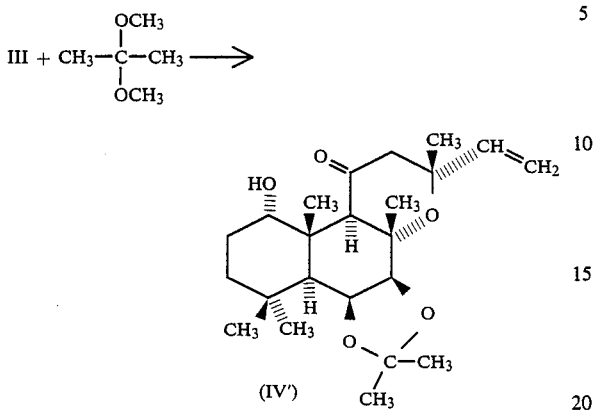

Typically, this reaction is conducted by dissolving compound III in a large excess of 2,2-dimethoxypropane, adding a small amount of pyridinium p-toluene sulfonate and stirring the mixture at reflux for a few days.

Compound IV' can be converted regioselectively to the enol ether of formula V' in substantially the same manner as in STEP C. Compound V' is believed to be novel.

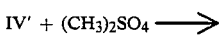

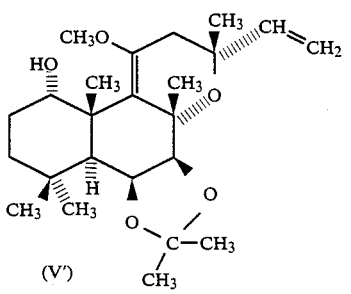

Compound V' can be oxidized stereoselectively to the compound of formula VI' in substantially the same manner as in STEP D. Compound VI' is believed to be novel.

Compound VI' can be hydrolyzed to afford the compound of formula VII' in substantially the same manner as in STEP E, and thereafter the protective group of compound VII' can be removed in substantially the same manner as in STEP F to afford the aforementioned compound VIII.

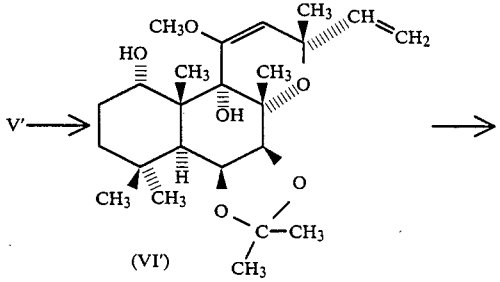

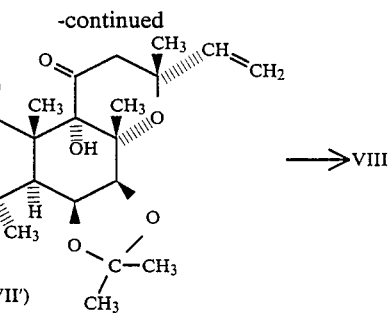

People skilled in the art will appreciate that not only compound I, but also compounds V through VIII as well as V' through VII' are useful for preparing various pharmacologically useful derivatives therefrom. Thus, the present invention is not limited to the preparation of compound I, but it includes methods for preparing compounds V through VIII and V' through VII' as other aspects of the invention.

Moreover, compounds V, VI, V' and VI' are believed to be novel and hence the present invention includes these compounds as still another aspect of the invention.

The following examples are given for illustrative purposes and are not to be construed as limiting the invention disclosed herein. All temperatures are given in degrees Celsius.

EXAMPLE 1

8,13-Epoxy-1α, 6β, 7β-trihydroxylabd-14-en-11-one

To a stirred solution of 2.0 g of 7-acetoxy-1α, 6β-dihydroxy-8,13-epoxylabd-14-en-11-one in 50 ml of reagent grade methanol (undried) was added 1.0 g of potassium carbonate. The mixture was stirred at room temperature for 3.0 hours and thereafter partitioned between ether (50 ml) and water (50 ml). The organic phase was removed and the aqueous phase was extracted with ether (3×50 ml). The combined organic phases were dried over magnesium sulfate. Filtration and removal of solvent in vacuo gave 1.768 g of crystals, mp 76-78° C. (recrystallized, mp 83-85° C.).

ANALYSIS: Calculated for $C_{20}H_{32}O_5$: 68.15%C 9.15%H. Found: 68.42%C 9.42%H.

EXAMPLE 2

8,13-Epoxy-1α, 6β, 7β-trihydroxylabd-14-en-11-one-6,7-carbonate

To a solution of 300 mg of 8,13-Epoxy-1α, 6β, 7β-trihydroxylabd-14-en-11-one in 25 ml of dry toluene and 1 ml of triethylamine was added 169 mg of 1,1'-carbonyldiimidazole. The solution was heated to reflux under nitrogen with stirring. A new spot began to appear on TLC (thin layer chromatography) above the starting material.

After 72 hours, no further change in TLC was observed. The reaction mixture was diluted with 10 ml of toluene and filtered, and the filtrate was concentrated in vacuo. The residue was 6 chromatographed on silica gel using 3:1 hexane/ethyl acetate eluent to obtain 95.1 mg of solid, homogeneous by TLC.

ANALYSIS: Calculated for $C_{21}H_{30}O_6$: 66.64%C 7.99%H. Found: 66.38%C 8.31%H.

EXAMPLE 3

9,11-Dehydro-8,13-epoxy-11-methoxy-1α, 6β, 7β-trihydroxylabd-14-ene-6,7-carbonate To a suspension of potassium hydride (383 mg of 25% KH in oil) in 75 ml of dry THF (tetrahydrofuran) under nitrogen were added successively 0.15 ml of dimethyl sulfate and a solution prepared from 302 mg of 8,13-epoxy-1α, 6β, 7β-trihydroxylabd-14-en-11-one-6,7-carbonate and 2.0 ml of dry THF.

The reaction mixture was stirred at room temperature for 3.0 hours The mixture was then poured into 75 ml of aqueous ammonium hydroxide solution. The flask was washed with ether and the washings were added to the mixture. After stirring for 5 minutes, the mixture was extracted with ether. The combined organic phases were washed once with water and once with brine, and dried over anhydrous magnesium sulfate. The solvent was removed in vacuo and the residue chromatographed on silica using 4:1 hexane/ethyl acetate eluent, to provide 193.1 mg of foam, mp 123–125° C., homogeneous by TLC.

ANALYSIS: Calculated for $C_{22}H_{32}O_6$: 67.32%C 8.22%H. Found: 66.92%C 8.44%H.

EXAMPLE 4

11,12-Dehydro-8,13-epoxy-11-methoxy-1α, 6β, 7β, 9α-tetrahydroxylabd-14-ene-6,7-carbonate hemihydrate To a solution of 9,11-dehydro-8,13-epoxy-11-methoxy-1α, 6β, 7β-trihydroxylabd-14-ene-6,7-carbonate (100 mg) in 20 ml of dichloromethane were added successively a trace (about 3 mg) of anhydrous potassium carbonate and 65 mg of 85% meta-chloroperbenzoic acid. The mixture was stirred at room temperature for 48 hours, then poured into a mixture of 10 ml of saturated aqueous sodium bisulfite solution and 10 ml of saturated aqueous sodium bicarbonate solution. The aqueous phase was extracted with dichloromethane, and the combined organic phases were dried over anhydrous magnesium sulfate/potassium carbonate and concentrated in vacuo. The residual solid was recrystallized from hexane/ethyl acetate to provide 74.2 mg of product, mp 242–244° C., homogeneous by TLC.

ANALYSIS: Calculated for $C_{22}H_{32}O_7 \cdot 1/2H_2O$: 63.29%C 7.96%H. Found: 63.14%C 8.41%H.

EXAMPLE 5

8,13-Epoxy-1α, 6β, 7β, 9α-tetrahydroxylabd-14-en-11-one-6,7-carbonate

To a solution of 13 mg of 11,12-dehydro-8,13-epoxy-11-methoxy-1α, 6β, 7β, 9α-tetrahydroxylabd-14-en-14-en-6,7-carbonate hemihydrate in 6 ml of tetrahydrofuran was added 2 ml of 3N aqueous hydrochloric acid. The mixture was stirred at room temperature for 18 hours at which time TLC showed complete conversion of the starting material. The mixture was poured into 25 ml of saturated aqueous sodium bicarbonate solution and extracted with ether. The combined organic phases were dried over anhydrous magnesium sulfate and concentrated to provide 12 mg of 8,13-epoxy-1α, 6β, 7β, 9α-tetrahydroxylabd-14-en-11-one-6,7-carbonate as a solid.

EXAMPLE 6

8,13-Epoxy-1α,6β, 7β, 9α-tetrahydroxylabd-14-en-11-one

To a solution of 8,13-epoxy-1α, 6β, 7β, 9α-tetrahydroxylabd14-en-11-one-6,7-carbonate (5.0 mg) in 5 ml of methanol was added 1 ml of saturated aqueous sodium bicarbonate solution. The mixture was stirred at room temperature for 48 hours, diluted with water and extracted with ether. The combined organic phases were dried over anhydrous magnesium sulfate/potassium carbonate and concentrated to provide 4.2 mg of 8,13-epoxy-1α, 6β, 7β, 9α-tetrahydroxylabd-14-en-11-one.

EXAMPLE 7

7β-Acetoxy-8,13-epoxy-1α, 6β, 7β, 9α-trihydroxylabd-14-en-11-one

To a solution of 8,13-epoxy-1α, 6β, 7β, 9α-tetrahydroxylabd14-en-11-one (27 mg) in 4 ml of anhydrous pyridine cooled to 0°, 2 ml of acetic anhydride was added with stirring. Stirring was continued at 0° for 5 hours, at which time no starting material was visible by TLC 2:1 hexane/ethyl acetate. The mixture was diluted with 50 ml of water, which caused a white solid to precipitate The crystals were collected, washed with a small amount of water and dried in vacuo to provide 25 mg of white crystals. These were shown by NMR to be 7β-acetoxy-8,13-epoxy-1α, 6β, 7β, 9α-trihydroxylabd-14-en-11-one contaminated with less than 10% of 1α, 7β-diacetoxy-8,13-epoxy-6β, 9α-dihydroxylabd-14-en-11-one. Recrystallization from hexane provided 17.6 mg of 7β-acetoxy-8,13-epoxy-1α, 6β, 9α-trihydroxylabd-14-en-11-one, pure by TLC.

EXAMPLE 8

8,13-Epoxy-1α, 6β, 7β-trihydroxy-labd-14-en-11-one-6,7-dimethyl

To a solution of 250 mg of 8,13-epoxy-1α, 6β, 7β-trihydroxy-labd-14-en-11-one in 50 ml of 2,2-dimethoxypropane was added one crystal of pyridinium p-toluene-sulfonate. The solution was heated to reflux with stirring under a $CaSO_4$ drying tube. After 72 hours no starting material was observed by TLC. The mixture was allowed to cool to room temperature and thereafter poured into saturated aqueous sodium bicarbonate solution and extracted with 4×50 ml of ether. The combined organic extracts were dried over anhydrous magnesium sulfate, filtered and concentrated in vacuo. The residual solid was chromatographed on silica using hexane/ethyl acetate (4:1) as eluent, to give 179 mg of product as a foam, homogeneous by TLC (1:1 hexane/ethyl acetate).

ANALYSIS: Calculated for $C_{23}H_{36}O_5$: 70.37%C 9.24%H. Found: 69.78%C 9.16%H.

I claim:

1. A method of preparing the compound of the formula

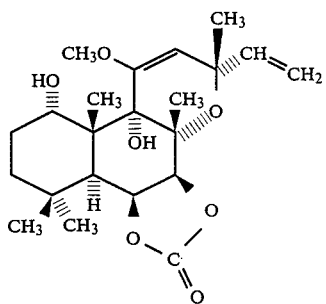

which comprises reacting the compound of the formula

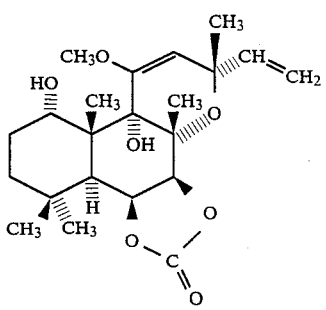

with a peroxy acid to afford said compound.

2. The method as described in claim 1, wherein the peroxy acid is m-chloroperbenzoic acid.

3. A method of preparing the compound of the formula

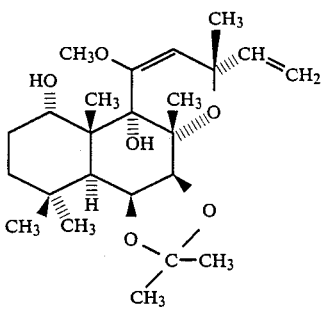

which comprises reacting the compound of the formula

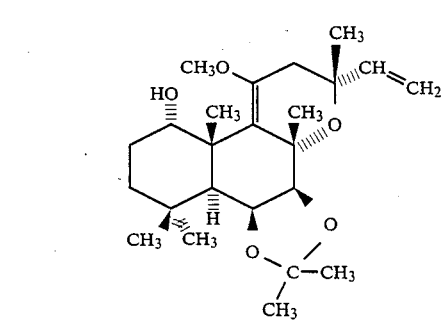

with a peroxy acid to afford said compound.

4. The method as defined in claim 3, wherein the peroxy acid is m-chloroperbenzoic acid.

* * * * *